US00PP26403P3

(12) United States Plant Patent
Infante

(10) Patent No.: US PP26,403 P3
(45) Date of Patent: Feb. 9, 2016

(54) NECTARINE DENOMINATED 'ANDES NEC-1'

(50) Latin Name: *Prunus persica*
Varietal Denomination: Andes Nec-1

(71) Applicant: VIVEROS ASOCIADOS CHILE LTDA. (ANA Chile-Andes Nursery Association), Paine (CL)

(72) Inventor: Rodrigo Infante, Paine (CL)

(73) Assignee: Viveros Asociados Chile LTDA. (ANA Chile-Andes Nursery Association), Paine (CL)

( * ) Notice: Subject to any disclaimer, the term of this patent is extended or adjusted under 35 U.S.C. 154(b) by 241 days.

(21) Appl. No.: 13/766,209

(22) Filed: Feb. 13, 2013

(65) Prior Publication Data

US 2014/0230108 P1 Aug. 14, 2014

(51) Int. Cl.
*A01H 5/08* (2006.01)

(52) U.S. Cl.
USPC ..... Plt./190
CPC ..... *A01H 5/0856* (2013.01)

(58) Field of Classification Search
USPC ..... Plt./190
CPC ..... A01H 5/0856; A01H 5/0837; A01H 5/08
See application file for complete search history.

(56) References Cited

PUBLICATIONS http://www.bayercropscience.cl/noticias/vernoticia.asp?id=2555 2011.*
http://www.bayercropscience.cl/noticias/vernoticia.asp?id=2555 (translated) 2011.*
Rodrigo Infante et al., "'Andes-1': An Early-maturing Clingstone Peach Cultivar for Canning and Fresh Market", HortScience, vol. 46, No. 3, 2011, pp. 499-500.

* cited by examiner

*Primary Examiner* — Kent L Bell
(74) *Attorney, Agent, or Firm* — Greer, Burns & Crain, Ltd.

(57) ABSTRACT

A new and distinct variety of clingstone nectarine tree denominated 'Andes Nec-1' that is similar to the nectarine 'Venus' in terms of its high postharvest potential, and firm in texture. The variety is distinguished from 'Venus' by producing fruit that is clingstone instead of freestone, has skin completely covered by red blush, and matures about two weeks earlier. The variety's harvest period is a week before the 'Fantasy' nectarine variety. Its fruit is solid red to red-purple blush over yellow flesh, with a round, symmetrical fruit shape.

3 Drawing Sheets

Species: *Prunus persica* (Nectarine).
Cultivar name: ANDES NEC-1.

This new cultivar resulted from controlled hybridization between the nectarine 'Venus' (♀) and the nectarine genotype 'Pr-07-J' (♂) performed in 2000 at Paine, Metropolitan Region, Chile (latitude −33°80'S, longitude −70°66'S, altitude 508 m above level). This tree was first asexually propagated on July 2005, and tested on a block of 20 cloned trees in the same experimental station at Paine. The new variety differs of his female progenitor 'Venus', due has a more round fruit, whereas 'Venus' is oblong, and also because the blush of 'Andes Nec-1' covers 100% of its surface, and 'Venus' seldom covers more than 60%. On regard of its male progenitor, the selection 'Pr-07-J', is less productive than 'Andes Nec-1', and in postharvest last no more than 21 days in good conditions, whereas 'Andes Nec-1' can maintain quality after 50 days in cold storage.

Distinctive characteristics of the variety: Semi upright plant growth, medium vigor, with abundant flowering during mid-season. Fruit round, symmetrical, yellow flesh, clingstone, blush is red, almost 100% coverage and solid. Harvest period a week before 'Fantasy'.

This cultivar main feature is a slow pulp softening rate commencing during the last two weeks before the commercial harvest. This characteristic enables delaying harvest, increasing in this way the size of the fruit and soluble solids content without affecting their postharvest life potential. Secondly it shows a high postharvest life potential, which can reach up to 50 days at 0° C. while maintaining its initial sensory quality. From a sensory point of view this is a cultivar of medium to high acidity with a balanced sweetness/acidity ratio and in general an average sensory quality. The cultivar is not susceptible to "chilling injury" and therefore can be used for exporting to distant markets.

Characterization of 'ANDES NEC-1' Nectarine

Figure 1:
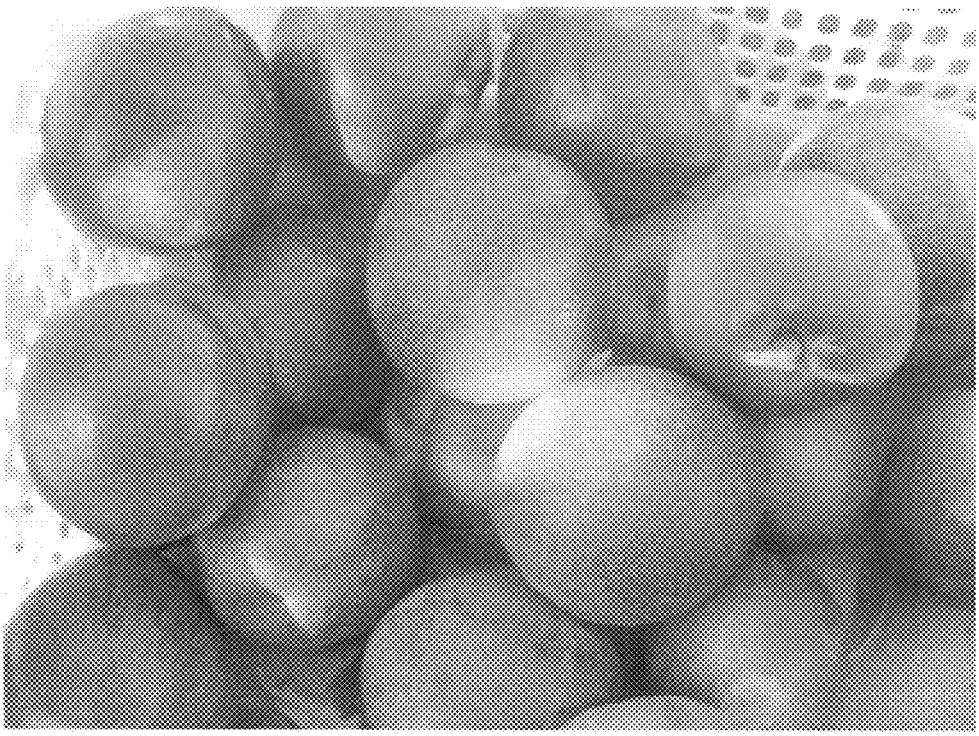
FIG. 1 shows the whole fruit in skin color and form.
Figure 2:
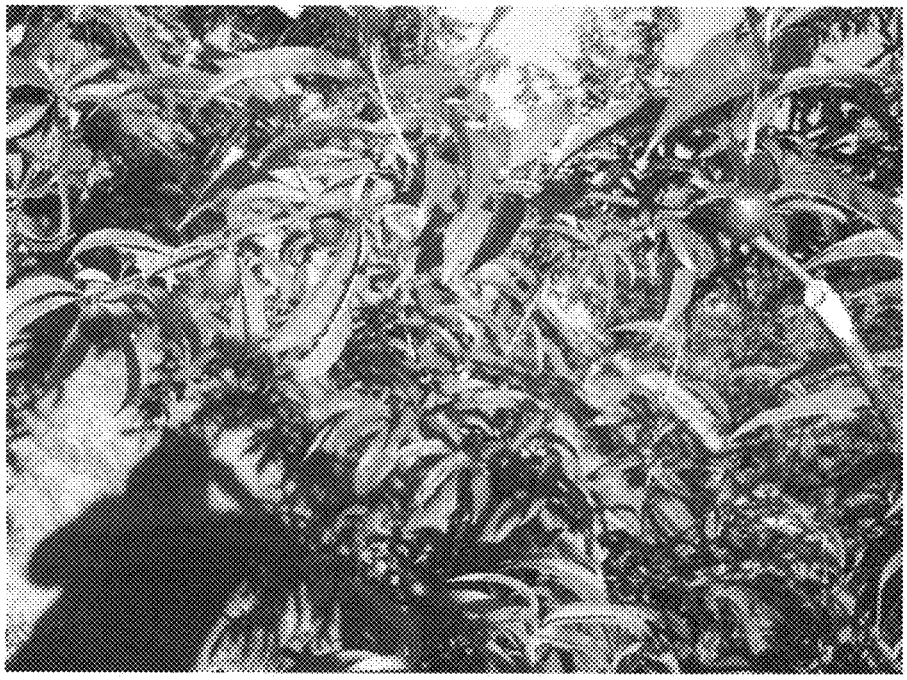
FIG. 2 shows a branch of the Andes NEC-1 tree, including a leaf.
Figure 3:
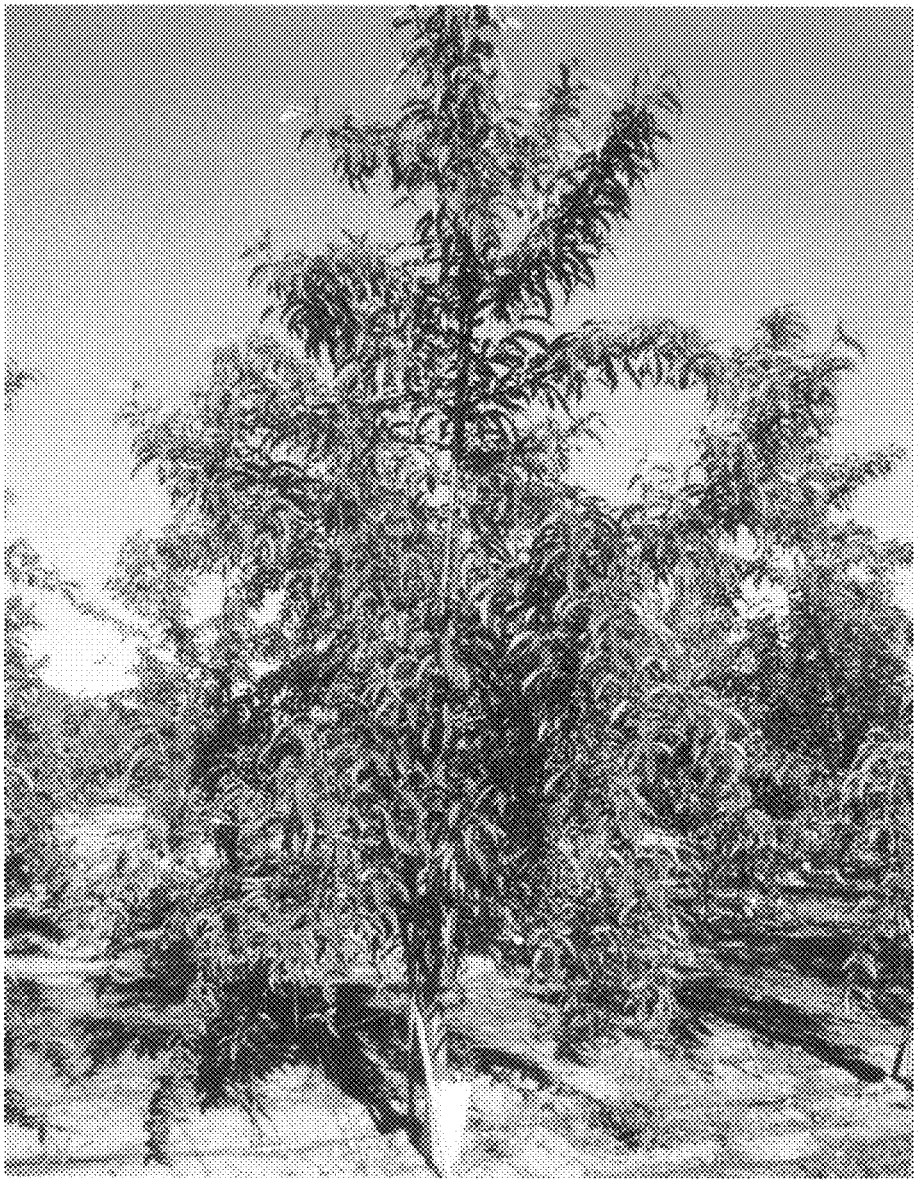
FIG. 3 shows the tree of 'Andes NEC-1.'

Tree:

1. *Size.*—Medium, similar to 'Bonanza'. An 8 year old tree is 4.5-4.8 m high shaped as an open vase, 2.4-3.0 of diameter.
2. *Vigor.*—Medium, similar to 'J.H. Hale'. Shoots reach 35 to 55 cm on regular spring/summer growing period.
3. *Habit.*—Horizontal, like 'Albertina'. It is well adapted to open vase training, but also for central leader training because the fruit weight forces shoots to a rather horizontal spreading.

4. *Flowering shoot thickness* (*excluding brindilles*).—Medium, similar to 'Redhaven'. The typical and observed flowering shoot diameter is 0.5-0.7 mm.
5. *Flowering shoot length of internodes.*—Medium, similar to 'Redhaven'. The typical and observed flowering shoot internode length is 2.5 to 3.2 cm.
6. *Flowering shoot.*—There is some anthocyanin coloration in the zone exposed to sunlight, reaching a reddish color, that in coordinates a*, b* and L* of the CIELab space color (McGuire, 1992) corresponds to 42.21, 9.8, and 11.62, respectively, but in the lower part of the shoot the anthocyanin coloration is weak, similar to 'Springtime', reaching a light brown color, that in coordinates a*, b* and L* of the CIELab space color (McGuire, 1992) corresponds to 39.17, 8.18, and 10.55, respectively. (McGuire, R. G. 1992. Reporting of Objective Color Measurements. Hortscience. 27(12): 1254-1255).
7. *Flowering shoot density of flower buds.*—Medium, similar to 'Michelini', reaching in an average year 20-30 flowers/30 cm long shoot.
8. *Flowering shoot.*—General distribution of flower buds: In groups of two or more per node, similar to 'Redhaven'.
9. *The trunk of an* 8-*year old tree.*—Shows a 10-12 cm diameter, measured on 50 cm above the ground, the bark texture is smooth, and the bark color is dark brown, that in coordinates a*, b* and L* of the CIELab space color (McGuire, 1992) corresponds to 25.16, 4.81, and 7.53, respectively.
10. *The primary branches diameter.*—Reach 5-6 cm in an 8-year old tree, and the color is light brown, that in coordinates a*, b* and L* of the CIELab space color (McGuire, 1992) corresponds to 45.26, −1.08, and 18.53, respectively.
11. *Vegetative buds shape and color.*—Acuminate, 4.5-6.5 mm length, color brown that in coordinates a*, b* and L* of the CIELab space color (McGuire, 1992) corresponds to 62.09, −5.11, and 29.64, respectively.

Flower:

12. *Type.*—It has a showy type, similar to 'Robin', reaching a whole diameter of 2.2 to 2.5 cm, and ovary is settled 0.3 to 0.4 cm low the calyx.
13. *Calyx color of inner side* (*opened flower, before petal fall*).—Similar to 'Robin', greenish yellow, that in coordinates a*, b* and L* of the CIELab space color (McGuire, 1992) corresponds to 62.01, 13.87, and 25.67, respectively.
14. *Corolla predominant color* (*inner side*).—Medium pink, similar to 'Fuzalode', that in coordinates a*, b* and L* of the CIELab space color (McGuire, 1992) corresponds to 62.01, 13.87, and 25.67, respectively.
15. *Petal shape.*—Round, similar to 'Springtime'.
16. *Petal size.*—Medium, similar to 'Robin', 1.0 to 1.2 cm diameter.
17. *Petals number.*—Five, similar to 'Redhaven'.
18. *Stamens position compared to petals.*—Above 0.5-1 mm, similar to 'Redhaven'.
19. *Stamen number and length.*—There are 32-38 stamens per flower in average 9-11 mm, of white-cream color, that in coordinates a*, b* and L* of the CIELab space color (McGuire, 1992) corresponds to 91.7, −1.42, and 9.46, respectively.
20. *Stigma position compared to anthers.*—Same level similar to 'Crimson Gold'.
21. *Pistil.*—There is normally 1 pistil per flower, 12-13 mm length and white-cream color, that in coordinates a*, b* and L* of the CIELab space color (McGuire, 1992) corresponds to 62.94, 3.77, and 9.32, respectively.
22. *Anthers pollen.*—Present and abundant, similar to 'Redhaven', in number 32 to 38, and the characteristic color is classified in coordinates a*, b* and L* of the CIELab space color (McGuire, 1992) corresponds to 83.13, −1.56, and 43.43, respectively.
23. *Ovary shape.*—Pubescence is absent, glossy skin, and round shape, the color is light green classified in coordinates a*, b* and L* of the CIELab space color (McGuire, 1992) corresponds to 55.09, 11.99, and 15.75, respectively.

Leaf:

24. *Leaf blade length.*—Long, reaching 12-13 cm long.
25. *Leaf blade width.*—Medium, reaching 3.0 to 3.6 cm width.
26. *Leaf blade ratio length/width.*—Medium, similar to 'Early Sungrand', reaching a ratio ranging from 3.4 to 4.
27. *Leaf blade shape in cross section.*—Flat, similar to 'Mayred'.
28. *Leaf blade recurvature of apex.*—Absent, similar to 'Merril Sundance'.
29. *Leaf blade angle at base.*—Acute, less than 90°, similar to 'Springtime'.
30. *Leaf blade angle at apex.*—Medium to acute, similar to 'Earlyred'.
31. *Leaf blade color.*—Green, classified in coordinates a*, b* and L* of the CIELab space color (McGuire, 1992) corresponds to 31.9, 4.38, and 9.02, respectively on the upper surface and light green in the lower surface, classified in coordinates a*, b* and L* of the CIELab space color (McGuire, 1992) corresponds to 38.89, 8.49, and 12.25, respectively. Similar to 'Robin'.
32. *Petiole length.*—Short, reaching 2-3 mm, similar to 'Redhaven'.
33. *Petiole nectaries.*—Present, in number 2-3 per leaf, similar to 'Redhaven'.
34. *Petiole shape of nectaries.*—Reniform, similar to 'Redhaven'.
35. *Petiole predominant number of nectaries.*—More than two, similar to 'Everts'.

Fruit:

36. *Fruit size.*—Medium, similar to 'Sunhaven', ranging between 180 to 245 g.
37. *Fruit shape* (*in ventral view*).—Round, similar to 'Redwing'. The observed fruit length parallel to the suture is 5.0 to 6.0 cm and width perpendicular to the suture is 5.1 to 5.8 cm.
38. *Fruit shape of pistil end.*—Plane, similar to 'Redhaven'.
39. *Fruit symmetry* (*viewed from pistil end*).—Symmetric, similar to 'Morettini'.
40. *Fruit prominence of suture.*—Weak, similar to 'Redhaven'.
41. *Fruit depth of stalk cavity.*—Shallow, similar to 'Robin', ranging between 5 to 7 mm.
42. *Fruit width of stalk cavity.*—Medium, 1.5 to 2.0 cm.
43. *Fruit ground color.*—Greenish yellow, classified in coordinates a*, b* and L* of the CIELab space color (McGuire, 1992) corresponds to 64.15, −11.7, and 29.72, respectively. Similar to 'Precoce de Hale'.

44. *Fruit over color.*—Present.
45. *Fruit hue of over color.*—Red, classified in coordinates a*, b* and L* of the CIELab space color (McGuire, 1992) corresponds to 46.67, 19.97, and 26.51, respectively. Similar to 'Red Diamond'.
46. *Fruit pattern of over color.*—Solid pattern, similar to 'Flavorcrest'.
47. *Fruit extent of over color.*—Large, reaching 98%.
48. *Fruit pubescence.*—Absent.
49. *Fruit thickness of skin.*—Medium, similar to 'Madame Girard'.
50. *Fruit adherence of skin to flesh.*—Strong, similar to 'Babygold 5'.
51. *Fruit firmness of pulp.*—Firm, 11.2 to 14 pounds when mature, similar to 'Redhaven'.
52. *Fruit ground color of flesh.*—Yellow, classified in coordinates a*, b* and L* of the CIELab space color (McGuire, 1992) corresponds to 51.71, 15.91, and 22.05, respectively.
53. *Fruit anthocyanin coloration directly under skin.*—Weakly expressed.
54. *Fruit anthocyanin coloration of flesh.*—Absent or very weakly expressed, similar to 'Robin'.
55. *Fruit anthocyanin coloration around stone.*—Absent or very weakly expressed, similar to 'Springtime'.
56. *Fruit texture of the flesh.*—Not fibrous, melting, and similar to 'Redhaven'.
57. *Fruit sweetness.*—Medium, ranging 11.2-13.5 Brix when mature, similar to 'Redhaven'.
58. *Fruit acidity.*—Medium, ranging between 1.2 to 1.6% malic acid when mature.

Stone:

59. *Stone size compared to fruit.*—Medium, ranging between 8 to 12 g, similar to 'Redhaven'.
60. *Stone shape* (*in lateral view*).—Obovate, similar to 'Rubidoux'. The length is 2.8 cm and width 1.4 cm.
61. *Stone intensity of brown color.*—Medium, classified in coordinates a*, b* and L* of the CIELab space color (McGuire, 1992) corresponds to 41.32, 9.15, and 15.08, respectively.
62. *Stone relief of surface.*—Similar to 'Madame Girard'.
63. *Stone grooves.*—Similar to 'Madame Girard'.
64. *Stone tendency of splitting* (*at peak harvest*).—Absent or very low, similar to 'Fairhaven'.
65. *Stone adherence to flesh.*—Present, similar to 'Sweet Gold'.
66. *Stone degree of adherence to flesh.*—Strong, similar to 'Vivian'.

Phenology:

67. *Time of leaf bud burst.*—Early, similar to 'Springtime'. On Southern Hemisphere is between $8^{th}$ to $12^{th}$ September.
68. *Time of beginning of flowering.*—Medium, similar to 'Redhaven'. On Southern Hemisphere is between $15^{th}$ to $25^{th}$ August.
69. *Duration of flowering.*—Short, similar to 'Philp', 6 to 8 days.
70. *Time of maturity for consumption.*—Medium, similar to 'Fairhaven'. On Southern Hemisphere is between $2^{th}$ to $12^{th}$ January.
71. *Tendency to preharvest.*—Absent, similar to 'Redhaven'.
72. *Pest/disease resistance/susceptibility.*—This genotype is not genetically resistant to any common pest and disease of peach, as Mildew, leaf curl, bacterial canker, aphids, thrips or, Oriental moth.
73. *Fruit characterization is on table* 1.

TABLE 1

Fruit characterization of nectarine 'Andes Nec-1'.

| SEASON | Harvest Date | Blush (%) | Equatorial Diameter | Firmness (Lb) Shoulders | Suture | Tip | Soluble solids (°Brix) |
|---|---|---|---|---|---|---|---|
| 2009-2010 | January 2 | 90 | 13.9 | 12.2 | 14.0 | 13.2 | 13.5 |
| 2010-2011 | January 12 | 90 | 12.2 | 11.2 | 12.3 | 12.4 | 13.2 |
| 2011-2012 | January 8 | 98 | 12.2 | 11.8 | 11.7 | 11.6 | 11.2 |

POSTHARVEST BEHAVIOR

At 50 days in cold storage +3 days at ambient temperature has good external appearance, no browning color or mealy texture, good taste and flesh firmness.

GENERAL TECHNICAL NOTES

Very good outward appearance. Excellent color coverage. Fruit round, no tip. High productivity. Good flavor.

CONCLUSIONS

After five years of evaluation, the variety continues to show its outstanding characteristics: very good productivity, good size, good flavor and good external appearance. High potential for export purposes because of exceptional post-harvest life.

Having thus described and illustrated the new variety of nectarine tree, I claim:

1. A new and distinct variety of nectarine tree, substantially as illustrated and described, that is similar to the nectarine 'Venus' in terms of its high postharvest potential, and firm in texture, but is distinguished therefrom by producing fruit that is clingstone instead of freestone in type, the skin is 100% covered by red blush, and that matures about two weeks earlier.

* * * * *